US005965521A

United States Patent [19]
Stephens et al.

[11] Patent Number: 5,965,521
[45] Date of Patent: Oct. 12, 1999

[54] PULSATILE DELIVERY OF LEPTIN RECEPTOR LIGANDS

[75] Inventors: Thomas W. Stephens; Mark L. Heiman, both of Indianapolis; José F. Caro, Carmel, all of Ind.

[73] Assignee: Eli Lilly Company, Indianapolis, Ind.

[21] Appl. No.: 08/804,668

[22] Filed: Feb. 25, 1997

[51] Int. Cl.$^6$ ............................. A61K 38/24; A01N 37/18
[52] U.S. Cl. .................................................. 514/2; 530/399
[58] Field of Search .................................. 530/399; 514/2

[56] References Cited

U.S. PATENT DOCUMENTS

| 4,172,124 | 10/1979 | Koprowski et al. |
| 4,196,265 | 4/1980 | Koprowski et al. |
| 4,271,145 | 6/1981 | Wands |

FOREIGN PATENT DOCUMENTS

| 0 743 321 | 5/1996 | European Pat. Off. |
| WO96/23515 | 1/1996 | WIPO |
| WO96/23517 | 1/1996 | WIPO |

OTHER PUBLICATIONS

Zhang et al., "Positional Cloning of the Mouse obese gene and its human homologue" *Nature* (1994) 372:425–432.
Murakami et al., "Cloning of Rat OBESE cDNA and Its Expression in Obese Rats$^+$" *Biochem. Biophys. Res Com.* (1995) 209:944–952.
Douillard, I.Y. and Hoffman, T., "Basic Facts About Hybridomas", in *Compendium of Immunology*, vol. II, L. Schwartz (Ed.) (1981).
Kohler, G. and Milstein, C., "Continous Cultures of Fused Cells Secreting Antibody of Predefined Specificity", *Nature* (1975) 256: 495–497.
Kohler, G. and Milstein, C., "Derivation of Specific Antibody–Producing Tissue Culture and Tumor Lines by Cell Fusion" *European Journal of Immunology* (1976) 6: 511–519.
Sinha, M.K. et al. "Nocturnal Rise of Leptin in Lean, Obese, and Non–Insulin–dependent Diabetes Mellitus Subjects" (1996) *J. Clin. Invest.* 97: 1344–1347.
M. Rosebaum et al., "Effects of Gender, Body Composition, and Menopause on Plasma Concentrations of Leptin" (1996) *J. of Clinical Endocrinology and Metabolism* 81:3424–3427, No. 9.

S. Hassink, MD et al., "Serum Leptin in Children with Obesity: Relationship to Gender and Development" (1996) *Pediatrics* 98:201–203, No. 98.
Byrne, M.M. et al. "Elevated Plasma Glucose 2 h Postchallenge Predicts Defects in β–Cell Function" *Am. J. Physiol.* (1996) 270:E572–579.
Stepens, T.W. et al. "The Role of Neuropeptide Y in the Antiobesity Action of the obese Gene Product"*Nature* (1995) 377:530–532.
Bolton, A.F. & Hunter, W.M. "The Labelling of Proteins to High Specific Radioactivities by Conjugation to a $^{125}$ I–Containing Acylating Agent" *Biochem. J.* (1973) 133:529–539.
Van Cauter, E., & Honicky, E. "Pulsatility of Pituitary Hormones" *Exp. Brain Res.* (1985) 12(suppl):41–60.
Sturis, J. "Computer Model for Mechanisms Underlying Ultradian Oscillations of Insulin and Glucose" *Am. J. Physiol.* (1991) 260:E801–809.
MacDougald, O.A. et al. "Regulated Expression of the Obese Gene Product (leptin) in White Adipose Tissue and 3T3–L1 Adipocytes" *Proc. Natl. Acad. Sci.* (*USA*) (1995) 92:9034–9037.
Consideine, R.V., et al. "Serum Immunoreactive–Leptin Concentrations in Normal–Weight and Obese Humans" *New Eng. J. Med.*(1996) 334:292–295.
Maffei, M. et al. "Leptin Levels in Human and Rodent: Measurement of Plasma Leptin and ob RNA in Obese and Weight–Reduce Subjects" *Nature Medicine* (1995) 1:1155–1161.
Kolaczynski, J.W. et al. (1996) *Diabetes* 43(Supp. 1): (Abstract).
Sinha et al. Biochem Biophy. Res Comm. vol. 228 No. 3, pp. 733–738 (1996).

*Primary Examiner*—Paula K. Hutzell
*Assistant Examiner*—Geetha P. Bansal
*Attorney, Agent, or Firm*—Burns, Doane, Swecker & Mathis, L.L.P.

[57] ABSTRACT

This invention provides a method for optimizing the administration of leptin receptor ligands to a mammal in need of such treatment. More specifically, this invention provides an improved method of delivering leptin receptor ligands to a mammal in need of such treatment comprising pulsatile or peak delivery of leptin receptor ligands to treat obesity and related conditions, including hyperglucocorticoidinemia, fertility or delayed puberty, and/or growth hormone deficiencies.

2 Claims, No Drawings

SEQUENCE LISTING

```
<160> NUMBER OF SEQ ID NOS: 1

<210> SEQ ID NO 1
<211> LENGTH: 146
<212> TYPE: PRT
<213> ORGANISM: Unknown
<220> FEATURE:
<221> NAME/KEY: PEPTIDE
<222> LOCATION: ()..)
<223> OTHER INFORMATION: Amino acid at position 28 is Xaa wherein Xaa is
      Gln or absent.
<220> FEATURE:
<223> OTHER INFORMATION: Description of Unknown Organism:proteins of
      preferred leptin analogs

<400> SEQUENCE: 1

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Xaa Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95
```

```
His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

PULSATILE DELIVERY OF LEPTIN RECEPTOR LIGANDS

BACKGROUND OF THE INVENTION

1. Field of the Invention

This invention relates generally to a method for optimizing the administration of leptin receptor ligands to a mammal in need of such treatment. More specifically, this invention relates to an improved method of delivering leptin receptor ligands to a mammal in need of such treatment comprising pulsatile or peak delivery of leptin receptor ligands to treat obesity and related conditions, including hyperglucocorticoidemia, fertility or delayed puberty, and/or growth hormone deficiencies.

2. Description of the Related Art

A diurnal rhythm has been demonstrated with leptin levels peaking near midnight to early morning hours in either lean or obese subjects. Pulsatility has recently been reported to exist in leptin levels with ~32 pulses/24 hour period (Licino, J. et al. (1996) Periodicity and pulsatility of circulating leptin levels in men. Submitted). This pulsatility suggests some coordinated synthesis and release of leptin by adipose tissue depots, although a mechanism for such coordination is unknown. Increased leptin with prolonged overfeeding may be the result of alterations in fat stores (Kolaczynski, J. W. et al (1996) Response of leptin to short term and prolonged overfeeding in humans. *J. Cln. Endo. Metab.* Submitted). As a result, leptin levels are altered according to several overlapping biological rhythms. These biorhythms may be key to optimal leptin action as with other hormones, e.g., LHRH, where continual stimulation yields opposite results to pulsatile stimulation.

Since chronic dosing at high levels of receptor agonists can lead to desensitization, it is possible that leptin resistance evolves from chronic hyperleptinemia.

SUMMARY OF THE INVENTION

Accordingly, a major object of the present invention is to provide an improved method of delivering leptin receptor ligands to a mammal in need of such treatment comprising pulsatile or peak delivery of leptin receptor ligands to treat obesity, hyperglucocorticoidemia, fertility or delayed puberty, or growth hormone deficiencies.

More specifically, the present invention provides an improved method of leptin therapy comprising timing the peak of leptin administration to coincide with the normal circadian peak of leptin release. The present invention also provides an improved method of leptin therapy comprising pulsatile administration of leptin at approximately a physiological frequency.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

This invention arose from a desire of the inventors to improve on previously available methods of administering leptin therapy. More specifically, the inventors sought to provide an improved treatment for obesity and related conditions, in particular a treatment which would prevent or inhibit the development of leptin resistance in a mammal in need of such treatment.

Since plasma leptin levels have been found to peak during the night in humans near midnight and to show pulsatility with a frequency of less than one hour, optimal leptin delivery requires appropriately timed administration. Thus, administration of leptin or leptin mimetics at the normal midnight peak, pulsatile delivery at frequencies similar to those found in normal physiological states yields optimal benefits in the treatment of obesity.

The inventors have found that timed and/or pulsatile administration of leptin receptor ligands, in particular leptin receptor agonists, may be advantageously used in place of prior art methods of administering leptin receptor ligands. Since plasma leptin levels have been found to peak during the night in humans near midnight and to show pulsatility with a frequency of less than one hour, optimal leptin delivery requires appropriately timed administration. Thus, administration of leptin or leptin mimetics at the normal midnight peak, pulsatile delivery at frequencies similar to those found in normal physiological states yields optimal benefits in the treatment of obesity.

The phrases "receptor ligands", "receptor agonists", and "receptor antagonists" used herein are understood to refer to pharmacologically active compounds, and to salts thereof. Preferred leptin receptor agonists for use in the present invention include endogenous leptin (i.e., endogenous OB protein—the protein produced from the obesity gene following transcription and translation and deletion of introns, translation to a protein and processing to the mature protein with secretory signal peptide removed, e.g., from the N-terminal valine-proline to the C-terminal cysteine of the mature protein). The mouse OB protein and human OB protein are published in Zhang et al., *Nature* 372:425–432 (1994). The rat OB protein is published in Murakami et al., *Biochem. Biophys. Res. Com.* 209:944–952 (1995). The porcine and bovine OB genes and proteins are disclosed in EP 0 743 321, the contents of which are incorporated by reference. Various primate OB genes and proteins are disclosed in U.S. application Ser. No. 081710,483, the contents of which are incorporated by reference. Also preferred for use in the present invention are leptin analogs, preferably leptin analogs having one or more amino acid substitution, more preferably less than five and most preferably less than three substitutions. Particularly preferred leptin analogs for use in the present invention include proteins disclosed by Basinski et al., in WO 96/23515 and WO 96/23517 (the contents of which are incorporated by reference), of the Formula (I):

```
                                                              SEQ ID NO: 1
 1                  5                    10               15
Val Pro Ile Gln Lys Val Gln Asp Asp Thr Lys Thr Leu Ile Lys 20                   25               30
Thr Ile Val Thr Arg Ile Asn Asp Ile Ser His Thr Xaa Ser Val 35                   40               45
Ser Ser Lys Gln Lys Val Thr Gly Leu Asp Phe Ile Pro Gly Leu 50                   55               60
His Pro Ile Leu Thr Leu Ser Lys Met Asp Gln Thr Leu Ala Val 65                   70               75
Tyr Gln Gln Ile Leu Thr Ser Met Pro Ser Arg Asn Val Ile Gln 80                   85               90
Ile Ser Asn Asp Leu Glu Asn Leu Arg Asp Leu Leu His Val Leu 95                   100              105
Ala Phe Ser Lys Ser Cys His Leu Pro Trp Ala Ser Gly Leu Glu 110                  115              120
Thr Leu Asp Ser Leu Gly Gly Val Leu Glu Ala Ser Gly Tyr Ser 125                  130              135
Thr Glu Val Val Ala Leu Ser Arg Leu Gln Gly Ser Leu Gln Asp 140                  145
Met Leu Trp Gln Leu Asp Leu Ser Pro Gly Cys
``` or pharmaceutically acceptable salts thereof, wherein:

Xaa at position 28 is Gln or absent;

said protein having at least one of the following substitutions:

Gln at position 4 is replaced with Glu;
Gln at position 7 is replaced with Glu;
Asn at position 22 is replaced with Gln or Asp;
Thr at position 27 is replaced with Ala;
Xaa at position 28 is replaced with Glu;
Gln at position 34 is replaced with Glu;
Met at position 54 is replaced with methionine sulfoxide, Leu, lle, Val, Ala, or Gly;
Gln at position 56 is replaced with Glu;
Gln at position 62 is replaced with Glu;
Gln at position 63 is replaced with Glu;
Met at position 68 is replaced with methionine sulfoxide, Leu, lle, Val, Ala, or Gly;
Asn at position 72 is replaced with Gln, Glu, or Asp;
Gln at position 75 is replaced with Glu;
Ser at position 77 is replaced with Ala;
Asn at position 78 is replaced with Gln or Asp;
Asn at position 82 is replaced with Gln or Asp;
His at position 97 is replaced with Gln, Asn, Ala, Gly, Ser, or Pro;
Trp at position 100 is replaced with Ala, Glu, Asp, Asn, Met, lle, Phe, Tyr, Ser, Thr, Gly, Gln, Val, or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp;
Gly at position 118 is replaced with Leu;
Gln at position 130 is replaced with Glu;
Gln at position 134 is replaced with Glu;
Met at position 136 is replaced with methionine sulfoxide, Leu, lle, Val, Ala, or Gly;
Trp at position 138 is replaced with Ala, Glu, Asp, Asn, Met, lle, Phe, Tyr, Ser, Thr, Gly, Gln, Val, or Leu; or
Gln at position 139 is replaced with Glu.

In addition, compounds for use in the present invention are optionally substituted with a functional group. Any art-recognized functional group which does not eliminate or significantly reduce the compound's ability to bind to leptin receptors are contemplated, including, but not limited to, ester, amide, acid, amine, alcohol, ether, thioether, etc. Solvates, e.g., hydrates of the compounds useful in the methods of the present invention, are also included within the scope of the present invention. Methods of salvation to produce such solvates are generally known in the art.

Pharmaceutical salts of the leptin receptor agonists and antagonists suitable for administration by a variety of routes are known in the art and need not be described herein in detail. Examples of pharmaceutically acceptable salts of the compounds and derivatives thereof according to the invention, include base salts, e.g., derived from an appropriate base. Pharmaceutically acceptable salts of an acid group or an amino group include, but are not limited to, salts of organic carboxylic acids such as acetic, lactic, tartaric, malic, isothionic, and lactobionic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as $Na^+$.

In a further embodiment of the present invention comprises a method for inhibiting the effects of endogenous leptins by peak or pulsatile administration of antibodies to endogenous leptins to a mammal in need of such treatment. Such antibodies may be monoclonal or polyclonal antibodies to leptin receptor agonists, or to antigenic parts thereof.

Both polyclonal and monoclonal antibodies to leptin receptor agonists are obtainable by immunization of an animal with purified leptin receptor agonists, purified recombinant leptin receptor agonists, fragments of these proteins, or purified fusion proteins of leptin receptor agonists, with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual,* Cold Spring Harbor Laboratory, Cold Spring Harbor, N.Y., 726 pp.

Polyclonal sera are relatively easily prepared by injection of a suitable laboratory animal with an effective amount of purified leptin receptor agonists, or parts thereof, collecting serum from the animal, and isolating specific sera by any of the known immunoadsorbent techniques. Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas", in *Compendium of Immunology,* Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.

A still further part of this invention is a pharmaceutical composition of matter suitable for peak or pulsatile administration that comprises at least one of the leptin receptor agonists or antagonists described above, mixtures thereof, and/or pharmaceutical salts thereof, and a pharmaceutically-acceptable carrier therefor. Such compositions are prepared in accordance with accepted pharmaceutical procedures, for example, as described in *Remington's Pharmaceutical Sciences,* seventeenth edition, ed. Alfonso R. Gennaro, Mack Publishing Company, Easton, Pa. (1985).

For therapeutic use in the method of the present invention, a leptin receptor agonist or antagonist, or its salt, can be conveniently administered in the form of a pharmaceutical composition containing one or more leptin receptor agonists or antagonists, or salts thereof, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

Compounds for use in the method of the present invention, or salts thereof, may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous, intradermal, and transdermal) administration, with topical ointment formulations, and formulations appropriate for oral administration, being preferred.

For timed peak delivery of leptin receptor ligands a device capable of delivering a peak action, such as a pen, syringe, pulmonary, or fast-acting oral delivery system is preferred. For pulsatile delivery of leptin receptor ligands, a device capable of delivering pulses, such as a pump, engineered cell line, time release oral or pulmonary formulation is preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

A compound for use in the present invention may be present in the composition in an broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The dosage of the leptin receptor agonists or antagonists, pharmaceutically acceptable salts thereof, or mixtures thereof, administered to a patient according to the present invention will vary depending on several factors, including, but not limited to, the age, weight, and species of the patient, the general health of the patient, the severity of the symptoms, whether the composition is being administered alone or in combination with other therapeutic agents, the incidence of side effects and the like.

In general, a dose suitable for application in the method of the present invention is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline, or orally administered as a bolus.

The active ingredient may be administered for therapy by any suitable routes, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Preferred is the oral route. Also preferred is the intravenous route. However, other routes may also be utilized depending the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including other therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective for the treatment of obesity and/or associated conditions in humans.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

Ultradian Oscillations of Leptin Secretion in Humans

In the present experiment we demonstrate ultradian oscillatory patterns of leptin secretion in humans with approximate frequency of four hours.

MATERIALS AND METHODS

Human Subjects.

A total of 36 human subjects participated in this study. Obesity was defined as a body mass index (BMI) >27.3 kg/m$^2$ for males and 27.8 kg/m$^2$ for females according to the National Institutes of Health Consensus Development Panel (*Ann. Intern Med.* 103:1073–77, 1995). Diabetics were classified following an oral glucose tolerance test according to the National Diabetes Data Group (*Diabetes* 23:1039–1056, 1979). All the subjects had no other disease except for obesity, diabetes, or mild hypertension. None of the subjects except the diabetics were in an active weight loss program or taking any drug known to alter carbohydrate metabolism For the present study two different experimental protocols were utilized.

Experimental Design for the First Protocol.

This protocol included 6 lean, 11 obese, and 5 obese diabetic subjects. Following an overnight fast, patients reported to the Clinical Research Unit at 7:00 AM. An indwelling IV catheter was placed. Fasting blood sample at 8:00 AM (zero time) was withdrawn, thereafter either 30 min., (immediately after meals), 60 min. (between meals), or 120 min (during sleep) blood samples were withdrawn until 7:30 AM the next day. Each subject received breakfast at 8:00 AM, lunch at 12:00 PM, dinner at 5:00 PM, and snack at 8:00 PM. Each subject was given an isocaloric diet (30 kcal/kg/day) comprised of 50% carbohydrates, 35% fat and 15% protein. The carbohydrate portion of the diet included complex carbohydrates and simple sugars. Total calories calculated for whole day consumption were distributed as 20% for breakfast, 30% for lunch, 40% for dinner, and 10% for a snack. The patients went to bed between 10:30 PM and midnight when television sets were turned off. Serum was separated from blood samples and stored frozen at −80° C. until assayed for insulin, glucose, and leptin levels. Utilizing the data generated with this protocol in this study, we have previously reported nocturnal rise of leptin secretion in lean, obese, and non-insulin dependent diabetes mellitus (Sinha, M. K. et al. (1996) *J. Clin. Invest.* 971344–1347).

Experimental Design for Second Protocol

A total of 10 normal healthy subjects (BMI: 35.87±2.00 kg/m$^2$) were admitted to the Clinical Research Center. Following an overnight fast, an intravenous sample catheter was introduced into the dorsal vein of one hand, and another catheter was introduced into the opposite hand. The hand with the sample catheter was maintained in the heating blanket to ensure arterialization of the venous sample. The subjects remained recumbent throughout the study. They were not allowed any food, but had free access to water. Following a 0 time fasting blood sample at 8:00 AM, oscillatory glucose infusion was started and further blood samples were withdrawn every 15 minutes over a 12 hour period. Plasma was separated and stored frozen at −80° C. until assayed for insulin, glucose, and leptin levels. The results of oscillatory glucose infusion on insulin secretion have been reported previously (Byrne, M. M. et al. (1996) *Am. J. Physiol.* 270:E572–579).

Assays

Serum leptin levels were determined by radioimmunoassay as previously described (Sinha, M. K., supra). Using recombinant human ob protein (RH leptin) synthesized in an *E. coli* expression system and purified to homogeneity (Stephens, T. W. et al. (1995) *Nature* 377:530–532) as a source of standard, radiolabeled ligand and antibody production. Recombinant human leptin was labeled with $^{125}$Iodine by the Bolton-Hunter method (Bolton, A. F & Hunter, W. M. (1973) *Biochem. J.* 133:529–539) followed by gel filtration on Sephadex G-25 column. One hundred μl of serum or recombinant human leptin (rh leptin) (standards 0–100 ng/ml) were incubated with anti-rh leptin rabbit serum (1:8000 dil) in 50 mM phosphate buffered saline, pH 7.4, containing 1.0% Triton X-100, 0.1% BSA and 0.01% sodium azide for 16 hours at 4° C. in a final volume of 400 μl. $^{125}$I-rh leptin (~30,000 cpm; ~30 μCi/μg specific activity) was then added for an additional 24 hours at 4° C. Thereafter bound leptin was immunoprecipitated with 100 μl of sheep anti-rabbit IgG serum (1:1 dil; Antibodies Inc., Davis, Calif.), 100 μl normal rabbit serum (1:50 dil; Gibco BRL, Gaithersburg, MD) and 100 μl of 10% polyethylene glycol (PEG 8000, Fisher Scientific Co.). After 20 min. incubation at 22° C. 1 ml assay buffer added and the tubes were centrifuged for 20 min. at 3400 rpm and the pellet counted in Packard 5000 gamma counter. In order to optimize the assay conditions, leptin standard curves were constructed with charcoal stripped serum from lean controls. Activated charcoal (C-5260: Sigma Chemical Co., St. Louis, Mo.) at 5% concentration (W/V) when incubated with serum for 16 hours at 4° C. effectively removed endogenous leptin. Serum leptin concentrations were calculated using unweighted four parametric logistic model. Our leptin radioimmunoassay characteristics were as follows: (a) Intra-assay coefficient of variation (CV): 8.93 at 5.2 ng/ml (n=12__, 3.31 at 17.8 ng/ml (n=13), 4.29 at 31.7 ng/ml (n=13), 5.78 at 47.1 ng/ml (n=24); (b) inter-assay CV: 15.9 at 3.31 ng/ml (n=7); 7.4 at 12.7 ng/ml (n=8); $ED_{50}$ 2.84±0.18 ng/ml (n=8); $ED_{50}$ 8.02±0.41 (n=8); and $ED_{50}$ 23.75±2.85 (n=8) and (e) Detection limit 0.39 ng/ml (n=8). Dose response curves showed linearity between 1.56–50 ng/ml concentrations. All serum samples from the same patient were run in triplicate in the same assay including same centrifugation step. In patients with high leptin levels, all the serum samples were assayed using 50 μl samples, i.e., at ½ dilution. Insulin levels were measured by double-antibody radioimmunoassay (Morgan, C. R. & Lazarow, A. (1963) *Diabetes* 12:115–116) and plasma glucose levels were measured with a glucose analyzer (Yellow Springs Instrument Co., Yellow Springs, Ohio).

Ultradian Oscillation Analysis

To identify significant peaks, each leptin profile was submitted to Ultra, a computer program for pulse detection (Sturis, J. et aL (1991) *Am. J. Physiol.* 260:E801–809). The general principle of the algorithm is to eliminate all peaks in plasma concentration for which either the increment or the decrement does not exceed a certain threshold related to measurement error. The threshold for pulse detection was set to a conservative value of two times the coefficient of variation (CV). We used intermediate CVs for respective profiles. For each profile, the threshold for pulse detection was $2(CV)/\sqrt{2}$. Absolute peak amplitude was evaluated as the difference preceding trough. Relative peak amplitude was defined as absolute peak amplitude divided by the value of the preceding trough.

Cross-correlation Analysis.

For all glucose and leptin profiles, linear trends were removed. For each pair of glucose and leptin profiles, coefficients of overall cross-correlation were then calculated between glucose and leptin at lags of 0, ±15, ±30, etc. up to ±150 min. Cross-correlation profiles from different studies were pooled using Fisher's z values. This procedure allowed the maximal coefficient of cross-correlation as well as the lag at which it occurred to be calculated.

Statistical Analysis

All results are expressed as mean ±SEM. Statistical significance was determined by simple regression analysis using Statview program on a Macintosh computer.

RESULTS

First Protocol.

In the first protocol, we obtained blood samples from 6 lean, 11 obese, and 5 obese NIDDM subject during their normal daily routines The frequency of blood sampling was every hour except immediately after meals, when it was every 30 minutes and during night, when blood samples were withdrawn at every two hour intervals. Table 1 summarizes the data of pulsatile patterns of leptin secretion from all subjects except two lean subjects with undetectable leptin levels. When the 24 hour leptin profiles from 20 lean and obese subjects with or without NIDDM were subjected to pulse analysis using ULTRA program, 1 to 7 oscillations were detected during 24 hour period. Average number of oscillations was 3.25±0.36 (mean ±SEM) per 24 hours. The periodicity was 10.01±1.47 hours. Absolute mean amplitude of leptin pulses was 11.26±2.06 ng/ml and relative mean amplitude was 0.52±0.06. As expected, a positive correlation (r=0.48, p<0.05) was observed between BMI and fasting (0800 hrs) circulating leptin levels among the study subjects. BMI and leptin levels also correlated significantly with mean absolute amplitude of the pulses (r=0.44, p<0.05) and r=0.96, b<0.0)1). However, no significant correlations were observed between BMI and either number of pulses, pulse periods, or relative amplitudes under these experimental conditions. From the 24 hour profiles of circulating leptin levels in 20 lean and obese subjects with or without NIDDM, it is apparent that leptin is secreted in an oscillatory manner.

Second Protocol

Since there was an indication of pulsatile secretion of leptin from less frequently sampled 24 hour profiles, we assayed plasma leptin levels in samples generated every 15 minutes from a previously published study were oscillatory infusion of glucose was given to 10 normal obese subjects following an overnight fast. Table 2 summarizes the data of leptin secretion and pulse analysis in those 10 subjects with 15 minute sampling over 12 hour period. In 10 study subjects used in the second protocol, significant positive correlation (r=0.71, p<0.025) was observed between BMI and fasting serum leptin levels. With 15 minute interval sampling protocol over a 12 hour period, 2 to 7 leptin pulses were observed with an average of 4.20±0.59 oscillations. The mean period for these oscillations was 3.44±0.49 hours. The averages for mean absolute amplitude and mean relative amplitude were 8.74±1.69 ng/ml and 0.28±0.03 ng/ml, respectively. The number of oscillations during a 12 hour period correlated significantly with BMI (r=0.94, p<0.001) and fasting leptin levels (r=0.78, p<0.01). In addition, the number of oscillations correlated positively with mean absolute amplitude (r=0.85, p<0.005). These results are consistent with the pulsatile leptin secretion in humans under these experimental conditions, i.e., with 15 minute blood sampling during oscillatory glucose infusion. FIG. 1 demonstrates ultradian oscillations in two of the 10 subjects as representative profiles. The cross-correlation analysis between glucose and leptin oscillations showed a lag of +45 minutes (corresponding to glucose leading leptin 45 min.) with a weak coefficient of cross-correlation (r=0.21, p<0.05). This would suggest that the ultradian glucose oscillations which normally exist but which were amplified in these experiments could affect the subsequent oscillations in circulating leptin levels by direct or indirect means.

DISCUSSION

Diurnal and/or ultradian oscillations are essential physiological characteristics of most endocrine hormones such as hypothalamus-pituitary axes, glucose regulation, steroid hormones, parathyroid system and renin-angiotensin systems and neurotransmitters (Van Cauter, E., & Honicky, E. (1985) *Exp. Brain Res.* 12(suppl):41–60). Recently, we demonstrated nocturnal rise of leptin secretion in humans which could be related to appetite suppression during sleep (Sinha, M. K. et al. (1996) *J. Clin. Invest.* 97:1344–1347). In the present example we demonstrate that in addition to diurnal rhythms of leptin secretion, ultradian oscillations for leptin secretion in humans. Even with less than optimal blood sampling protocol leptin pulses are detected during 24 hour periods (number of pulses: 3.25±0.36, mean relative amplitude: 0.52±0.06, n-20). Subsequently, we utilized blood samples which were obtained every 15 minutes over a 12 hour period during oscillatory glucose infusion following an overnight fast (Byrne, M. M. et al. (1996) *Am. J. Physiol.* 270:E572–579). With this 15 minute blood sampling protocol, a more discrete evidence about pulsatile nature of leptin secretion in humans is evident. During 12 hours, the number of leptin pulses was 4.2±0.59 with 3.44±0.49 hour periodicity and 0.280±0.03 mean relative amplitude. Both BMI and fasting leptin levels positively correlated with the number of pulses and a positive correlation is observed between the number of pulses and mean absolute amplitude. The cross-correlation results suggest that some glucose regulation of leptin secretion is possible. However, we have previously demonstrated no effects of meals on leptin secretion during 24 hour normal routines. There was no significant correlation with either meal time or circulating insulin or glucose levels and leptin levels (Sinha, M. K. et al. *J. Clin. Invest.* 97:1344–1347). Under different physiological conditions the ultradian oscillations for a variety of hormones ranges from 1 to 4 hours (Sturis, J. (1991) *Am. J. Physiol* 260:E801–809; Van Cauter, E. (1985) *Exp. Brain Res.* (suppl) 12:41–60). The periodicity for leptin secretion is similar to those previously reported for other endocrine hormones. A number of mechanisms modulating the amplitude and/or frequency of pulsatile or oscillatory hormonal release had been identified (Van Cauter, E., supra). The most significant ones include modulation by feedback of peripheral hormones and modulation by signals from the central nervous system. In addition the turnover of hormones, i.e., the rates of synthesis and degradation, also contribute towards the pulsatile pattern of hormonal secretion. For pulsatile secreting patterns it has been suggested that the endocrine glands are analogous to pacemakers (id.).

Unlike other endocrine glands which re discretely regulated through feedback mechanisms in a coordinated manner, at present it is difficult to perceive adipose tissue as an endocrine gland because of different fat depots with varying sizes and anatomical locations (id.). Unlike any other endocrine gland fat depots are not under the influence of any single predominant control mechanism. Circulating leptin levels are influenced by the degree of obesity, possibly by total fat mass, fasting, feeding, chronic hyperinsulinemia, hypercortisolemia, etc. (MacDougald, O. A. et al. (1995) *Proc. Natl. Acad. Sci.* (*USA*) 92:9034–9037; Considine, R. V., et al. (1996) *New Eng. J. Med.* 334:292–295; Maffei, M. et al. (1995) *Nature Medicine* 1:1155–1161; Kolaczynski, J. W. et al. (1996) *Diabetes* 43(Supp. 1): (Abstract)). However, acute regulation of circulating leptin levels which could explain our present observations of ultradian oscillations are not yet evident. Although the present observations were made with oscillatory glucose infusion, glucose per se could not be solely responsible for oscillatory leptin secretion since no significant correlations were observed between glucose and/or insulin and leptin levels during 24 hour periods of daily normal routines and meal ingestion (Sinha, M. K. et aL (1996) *J. Clin. Invest.* 97:1344–1347). We have also shown that glucose is not an independent modulator of leptin in humans (Considine, R. V. et al (1996) *New Eng. J. Med.* 334:292–295).

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. An improved method of delivering leptin receptor ligands to a mammal in need of such treatment comprising peak delivery of leptin receptor ligands at the time of normal circadian peak of leptin release to treat obesity, hyperglucocorticoidinemia, fertility or delayed puberty, or growth hormone deficiencies.

2. The method of claim 1, wherein the mammal is a human, and further wherein peak of leptin receptor ligand administration is approximately midnight.

* * * * *